United States Patent [19]
Pitt et al.

[11] 4,045,668
[45] Aug. 30, 1977

[54] METHOD AND APPARATUS FOR IMMISCIBLE LIQUIDS MEASUREMENT

[75] Inventors: Gillies D. Pitt, Harlow; Philip W. Black, Bishops Stortford, both of England

[73] Assignee: International Telephone and Telegraph Corporation, New York, N.Y.

[21] Appl. No.: 716,338

[22] Filed: Aug. 20, 1976

[30] Foreign Application Priority Data

Aug. 21, 1975 United Kingdom ............... 34778/75

[51] Int. Cl.² .............................................. G02B 5/14
[52] U.S. Cl. .................................. 250/227; 250/577; 350/96 R
[58] Field of Search .................... 250/577, 227, 574; 350/96 R, 96 B; 73/293

[56] References Cited
U.S. PATENT DOCUMENTS

| 3,448,616 | 6/1969 | Wostl | 250/577 |
| 3,553,666 | 1/1971 | Melone | 250/227 |
| 3,834,235 | 9/1974 | Bouton et al. | 73/293 |

*Primary Examiner*—David C. Nelms
*Attorney, Agent, or Firm*—A. Donald Stolzy

[57] ABSTRACT

A device for measuring the proportion of a first liquid in a lower refractive index second liquid with which the first liquid is immiscible, such as oil in water. An unclad optical fiber, having an index of refraction between those of the two liquids but at least equal to and not more than ten percent greater than that of the first liquid. A light energy source and detector are connected by the immersed fiber and the light energy transmission measured to determine liquid proportions.

8 Claims, 2 Drawing Figures

METHOD AND APPARATUS FOR IMMISCIBLE LIQUIDS MEASUREMENT

BACKGROUND OF THE INVENTION

1. Field of the Invention

The invention relates generally to the field of measurement of relative liquid percentages, and more particularly to measurement of the proportion of oil in water.

2. Description of the Prior Art

In the prior art, various devices are extant which address the oil-in-water measurement problem. These are either chemical, mechanical, or optical, a general class into which the present invention falls. Among these prior art devices are those which basically measure conductivity or some other electrical parameter or the actual density of the mixture. Many of these known techniques are cumbersome, time consuming or unduly sensitive to the presence of other soluble or insoluble materials. In ocean water measurements, where the need for instrumentation of the type is the greatest, the relative salinity is an interfering variable. Salinity can vary considerably between open ocean on the one hand, and estuaries and sheltered sea areas on the other hand. Certain prior art instruments for the same measurement purpose rely on ultra-violet fluorescence or infra-red absorption change as a result of oil content. Those provide relatively rapid determinations, but are sensitive to salinity changes necessitating frequent calibration when used on shipboard.

SUMMARY

The invention is generally applicable to measurement of the proportion of a first liquid dispersed in a lower refractive index second liquid with which the first is immiscible. A particular, but not necessarily exclusive application is the measurement of the presence of oil dispersed in water. Such measurements are required, for instance, for monitoring the discharge of ballast water from oil tenders. Other uses include monitoring tanker ballast water discharge.

According to the present invention there is provided apparatus and a basic method for measuring the proportion of a first liquid dispersed in a lower refractive index second liquid with which the first is immiscible. The method consists of monitoring the optical attenuation of a length of optical fiber having an unclad region immersed in the liquids dispersion, which unclad region has a refractive index greater than that of the second liquid but not more than 0.1 greater than that of the first liquid. Preferably the refractive index of the unclad region of fiber is either matched with, or is less than that of the first liquid. The light source is not necessarily an emitter in the visible part of the spectrum, it may alternatively be an IR or a UV emitter.

The measurement may be carried out on a discrete quantity sampling basis, or on a continuous flow basis. The continuous flow measurement may be made on a sample part or a larger total flow.

Accordingly the invention also provides apparatus for measuring the proportion of a first liquid dispersed in a lower refractive index second liquid with which the first is immiscible, which apparatus includes an optical fiber threading a measurement chamber containing the liquids dispersion. The optical fiber in the measurement chamber includes an unclad region the core refractive index of which is greater than that of the second liquid but not more than 0.1 greater than that of the first liquid. A light energy source is included for launching light energy into one end of the fiber and a detector is arranged for measuring the quantity (intensity) of light transmitted through the fiber to the other end. In another form of the device, the measurement chamber is replaced by a duct through which the liquids dispersion is caused to flow.

Preferably the liquids dispersion is ultrasonically vibrated in the vicinity of the unclad region of the optical fiber as this tends to promote uniformity of the dispersion and prevent an unrepresentatively large accumulation of the first liquid adherent to the fiber.

A feature of the present invention in its application to the measurement of oil in water is that it is comparatively insensitive to such variations in salinity as are likely to be encountered between the various ocean seas and coastal estuaries where there is fresh water dilution. For a ship-borne instrument, this has the advantage of reducing the frequency with which the instrument has to be recalibrated as compared with other aforementioned instruments of the type which rely upon the use of ultra-violet fluorescense and infra-red absorption techniques.

There follows a description of an oil-in-water measuring device embodying the invention in a preferred form. The description refers to the accompanying drawings.

DESCRIPTION OF THE PREFERRED EMBODIMENT

Figure 1:
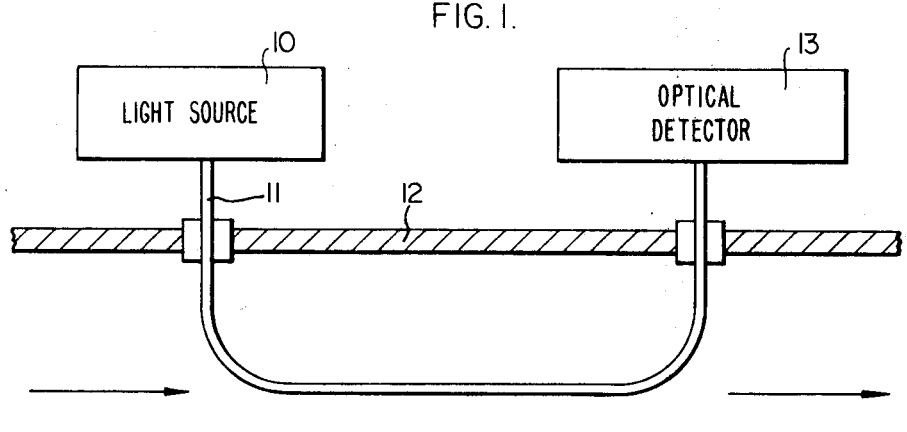
FIG. 1 is a diagram illustrating the components of a measuring device according to the invention.

The device of FIG. 1 consists essentially of a light source 10, a length of optical fiber 11, part of which threads through a pipe 12, and a calibrated optical detector 13. At least part of the length of that portion of the fiber threading the pipe 12 is unclad. The fiber has a refractive index greater than that of water but is either matched with or just less than that of the oil. When only water is present in the tube the water effectively acts as a cladding for the unclad length of fiber. If, however, oil is present and a globule of oil attaches itself to the fiber, light is radiated at this point through the globule and into the water with the result that the optical attenuation of the fiber is increased, i.e., the fiber becomes lossy through lateral radiation. The situation is illustrated in terms of ray optics in FIG. 2. There a globule of oil 20 is shown attached to the surface of an unclad section of optical fiber 21 which is immersed in water 22. A ray 23 is shown as propagating down the fiber by total internal reflection at each point never striking the fiber/water interface 27. Rays 24 and 25 are propagating at the same angle to the axis as ray 23, and therefore, in the absence of the globule 20, would propagate down the fiber in the same manner as ray 23. However, the refractive index of the globule is greater than that of the fiber and hence rays 24 and 25 are refracted into the globule through the interface 27. Then, owing to the rounded shape of the globule they strike the globule water interface 25 at less than the critical angle, and hence are refracted into the water. Other rays, such as ray 26 may strike the globule/water interface at angles greater than the critical angle and hence be reflected.

Some of these rays, such as ray 26, will therefore be reflected back into the fiber, but with an angle of incidence in the fiber less than the critical angle for the fiber/water interface, and hence will emerge from the side of the fiber opposite the globule. It will be appreciated however that some of the rays incident upon the globule will be reflected back into it at angles consistent with propagation down the fiber.

Figure 2:
FIG. 2 is a diagram illustrating how a globule of oil attached to the unclad region of fiber increases the fiber attenuation.
Figure 2:
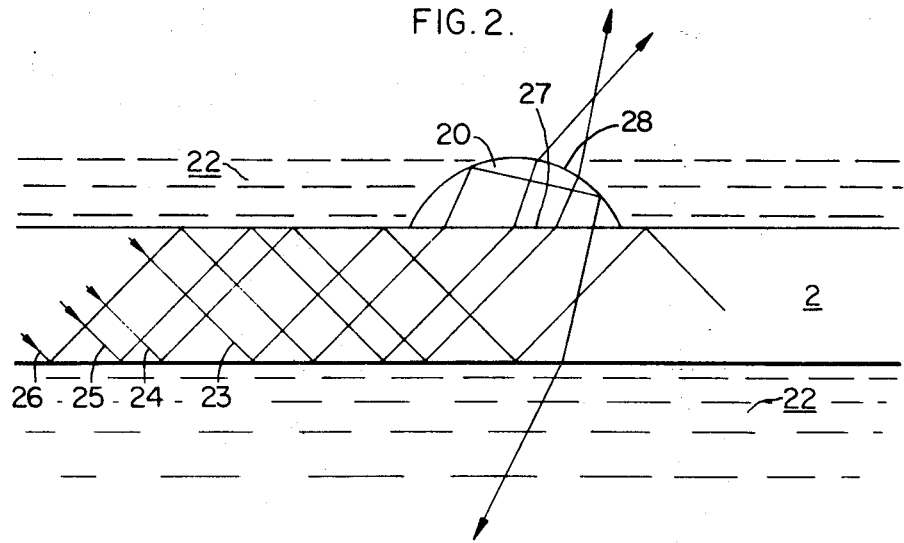

The ray geometry depicted in FIG. 2 represents the situation where the refractive index of the oil globule is greater than that of the fiber. Under these conditions some light is refracted at the interface between the fiber and the globule and a small proportion is reflected. If however the refractive index of the fiber is matched with that of the oil the reflected component vanishes and light passes undeviated through the fiber/oil globule interface. If the refractive index of the oil is less than that of the fiber there will be a measure of optical guidance provided by the fiber/oil interface. Provided that the refractive index of the oil is greater than that of the water, this guidance is less than that provided by the fiber/water interface, and hence the presence of an oil globule attached to the fiber will still attenuate light propagating in the fiber. This attenuation will be less than for the matched case, and for this reason it is not preferred to use a fiber whose refractive index exceeds that of the oil by more than about 10 percent.

Some means of cleaning the unclad region of fiber is normally in order to prevent an unrepresentatively large accumulation of oil on the fiber. One way of achieving this is to have a matched pair of pipes and fibers. Periodically the flow is transferred from one pipe to the other so that when one pipe is in use, the other may be flushed clean with a detergent mixture in preparation for its redeployment into the active water/oil mixture stream. An alternative method of cleaning involves placing one or more ultrasonic transducers 14 (FIG. 1) in the pipe in the vicinity of the fiber. This ultrasonic cleaning has the additional advantage of tending to promote a more uniform dispersion of the oil throughout the water.

The light source may be a laser such as for example a gallium arsenide laser, or it may be a broad band spectral emitter such as a quartz halogen lamp.

Silica is for many applications a suitable material from which to make the core of the optical fiber since its refractive index (1.45) lies significantly above that of pure water (1.33) or sea water (1.34 to 1.38) while being slightly below that of most mineral oils which typically have refractive indicies of at least 1.47. For some applications, however, it may be preferred to use optical fiber of plastics material of the types known in the fiber optics art.

To detect and distinguish between specific oil types, a set of fibers of different refractive index may be used and also the wavelength of the light propagating in the fiber may be selected from a particular part of the spectrum by filtering.

If a significant error is being introduced into a measurement by the presence of particulate contamination, such as paint scrappings, this can be allowed for by the use of a control loop with a fiber immersed in a flow from which the oil has been removed.

A feature of the instrument is that, since an optical fiber is involved, the display part of the instrument can readily be linked by optical fiber to a distant sensor part of the instrument. In this case, the optical fiber link may be continuation of the sensor fiber. Such a continuation may normally be provided with a cladding layer. Alternatively, the ends of the measurement fiber may be coupler fibers selected for lower transmission loss. Separation of the source and the detector from the sensor is useful in applications in which, for safety reasons, it is desired to keep the voltage supplies for the optical source and detector far removed from the environment of the sensor.

The sensitivity of the instrument can readily be of the order of a few parts per million of oil in water. For instance, using a 23 cm unclad length of 110 um diameter silica fiber propagating light from a HeNe laser operating at 6328 A, the detected power received at the far end of the fiber changed from 230 uW for pure water to 100 uW for water containing 100 parts per million dispersed oil of refractive index 1.4. Sensitivity can be increased not only by using a longer unclad length of fiber, but also by putting bends in the unclad region.

In an alternative form of apparatus, the pipe 12 is replaced by a measurement chamber into which a discrete quantity of the liquids dispersion is dispensed for batch type measurement.

It is to be understood that the foregoing description of a specific example of the invention is made by way of example only. The drawing and this description are to be as typical only are not to be regarded as a limitation on the scope of the invention.

What is claimed is:

1. A method of measuring the proportion of a first liquid dispersed in a lower refractive index second liquid with which the first is immiscible, comprising:
    monitoring the optical attenuation through a length of optical attenuation through a length of optical fiber having an unclad region immersed in the liquids dispersion, said which unclad region having a refractive index greater than that of the second liquid but not more than 0.1 greater than that of the first liquid.

2. A method as claimed in claim 1 comprising the additional step of ultrasonically vibrating said liquids dispersion in the vicinity of said unclad region of said fiber.

3. A method as claimed in claim 1 wherein the refractive index of the fiber is selected at or less than that of the first liquid.

4. A method according to claim 1 wherein the first liquid is oil and the second water.

5. A device for measuring the proportion of a first liquid dispersed in a lower refractive index second liquid with which said first liquid is immiscible, comprising:
    an optical fiber arranged to pass a measurement chamber containing the liquids dispersion which optical fiber includes an unclad region within said chamber, the core refractive index of said fiber being greater than that of said second liquid but not more than 0.1 greater than that of the first liquid;
    a light energy source arranged to launch light energy into one end of said fiber;
    an optical detector connected to the other end of said fiber for measuring the quantity of light transmitted by said fiber as a function of the proportion of said first liquid in said second liquid.

6. A device for measuring the proportion of a first liquid dispersed in a lower refractive index second liquid with which the first is immiscible, comprising:
    an optical fiber within a portion of a duct through which the liquids dispersion is caused to flow, said optical fiber including an unclad region within said duct, said fiber having a core refractive index greater than that of said second liquid but not more than 0.1 greater than that of said first liquid;

and means at first and second ends of said fiber respectively for transmitting light into said fiber and for measuring light emerging therefrom.

7. A device according to claim 5 wherein at least one ultrasonic transducer is located in said chamber in the vicinity of said unclad region of said optical fiber.

8. A device according to claim 6 in which at least one ultrasonic transducer is located in said chamber in the vicinity of said unclad region of said optical fiber.

* * * * *